(12) United States Patent
Yoshida

(10) Patent No.: US 10,638,968 B2
(45) Date of Patent: May 5, 2020

(54) SKIN GLOSS EVALUATION DEVICE, SKIN GLOSS EVALUATION METHOD, AND SKIN GLOSS EVALUATION PROGRAM

(71) Applicant: FUJIFILM Corporation, Tokyo (JP)

(72) Inventor: Naoko Yoshida, Ashigarakami-gun (JP)

(73) Assignee: FUJIFILM Corporation, Minato-Ku, Tokyo (JP)

( * ) Notice: Subject to any disclaimer, the term of this patent is extended or adjusted under 35 U.S.C. 154(b) by 4 days.

(21) Appl. No.: 15/908,894

(22) Filed: Mar. 1, 2018

(65) Prior Publication Data
US 2018/0184967 A1 Jul. 5, 2018

Related U.S. Application Data

(63) Continuation of application No. PCT/JP2016/071452, filed on Jul. 21, 2016.

(51) Int. Cl.
*G06K 9/00* (2006.01)
*A61B 5/00* (2006.01)
*G01N 21/25* (2006.01)
*G01N 21/57* (2006.01)
*G06T 7/00* (2017.01)

(52) U.S. Cl.
CPC ............ *A61B 5/442* (2013.01); *A61B 5/0077* (2013.01); *G01N 21/25* (2013.01); *G01N 21/57* (2013.01); *G06T 7/0012* (2013.01); *G06T 2207/30088* (2013.01)

(58) Field of Classification Search
None
See application file for complete search history.

(56) References Cited

U.S. PATENT DOCUMENTS 10,055,673 B2 * 8/2018 Burgos ................. G06K 9/3241
2005/0271295 A1 12/2005 Tabata et al.
(Continued)

FOREIGN PATENT DOCUMENTS

JP 2002-017689 A 1/2002
JP 2005-327009 A 11/2005
(Continued)

OTHER PUBLICATIONS

International Search Report for PCT/JP2016/071452, dated Oct. 18, 2016.
(Continued)

*Primary Examiner* — Samah A Beg
(74) *Attorney, Agent, or Firm* — Sughrue Mion, PLLC

(57) ABSTRACT

The present invention provides a gloss evaluation device, a gloss evaluation method, and a non-transitory computer readable recording medium storing gloss evaluation program capable of evaluating gloss of skin easily and highly accurately. In the gloss evaluation device of the present invention, a skin evaluation index calculation unit 5 calculates, as a skin evaluation index, a chroma difference between a portion in which it is easy for the gloss of the face of the subject to occur and a portion in which it is difficult for gloss to occur that are set as analysis ranges, and a luster and oiliness evaluation unit 6 evaluates luster and oiliness on the basis of the chroma difference.

12 Claims, 12 Drawing Sheets
(2 of 12 Drawing Sheet(s) Filed in Color)

(56) References Cited

U.S. PATENT DOCUMENTS

| | | | | |
|---|---|---|---|---|
| 2008/0294012 | A1* | 11/2008 | Kurtz | A61B 5/0059 600/300 |
| 2010/0185064 | A1* | 7/2010 | Bandic | A61B 5/0059 600/306 |
| 2011/0019029 | A1 | 1/2011 | Matsumoto et al. | |
| 2011/0301441 | A1* | 12/2011 | Bandic | A61B 5/0059 600/306 |
| 2014/0018634 | A1* | 1/2014 | Baumann | G06Q 30/02 600/300 |
| 2015/0105635 | A1* | 4/2015 | Yoshida | G01N 21/4795 600/306 |
| 2015/0287191 | A1* | 10/2015 | Koruga | A45D 44/00 382/128 |
| 2016/0106198 | A1 | 4/2016 | Yoshida et al. | |
| 2016/0143595 | A1* | 5/2016 | Yoshida | A61B 5/7275 600/306 |
| 2017/0079599 | A1* | 3/2017 | Yoshida | G06T 7/40 |
| 2017/0336199 | A1* | 11/2017 | Masuda | A61K 8/368 |
| 2017/0347939 | A1* | 12/2017 | Tang | A61B 5/00 |
| 2018/0000349 | A1* | 1/2018 | Yoshida | A61B 5/107 |
| 2019/0212136 | A1* | 7/2019 | Masuda | G01B 11/30 |

FOREIGN PATENT DOCUMENTS

| | | |
|---|---|---|
| JP | 2011-044132 A | 3/2011 |
| JP | 2011-130808 A | 7/2011 |
| JP | 2014-046698 A | 3/2014 |
| WO | 2014/196532 A1 | 12/2014 |

OTHER PUBLICATIONS

Written Opinion dated Oct. 18, 2016, issued by the International Bureau in counterpart Application No. PCT/JP2016/071452.

International Preliminary Report on Patentability issued from the International Bureau in counterpart International Application No. PCT/JP2016/071452, English version, dated Mar. 13, 2018.

* cited by examiner

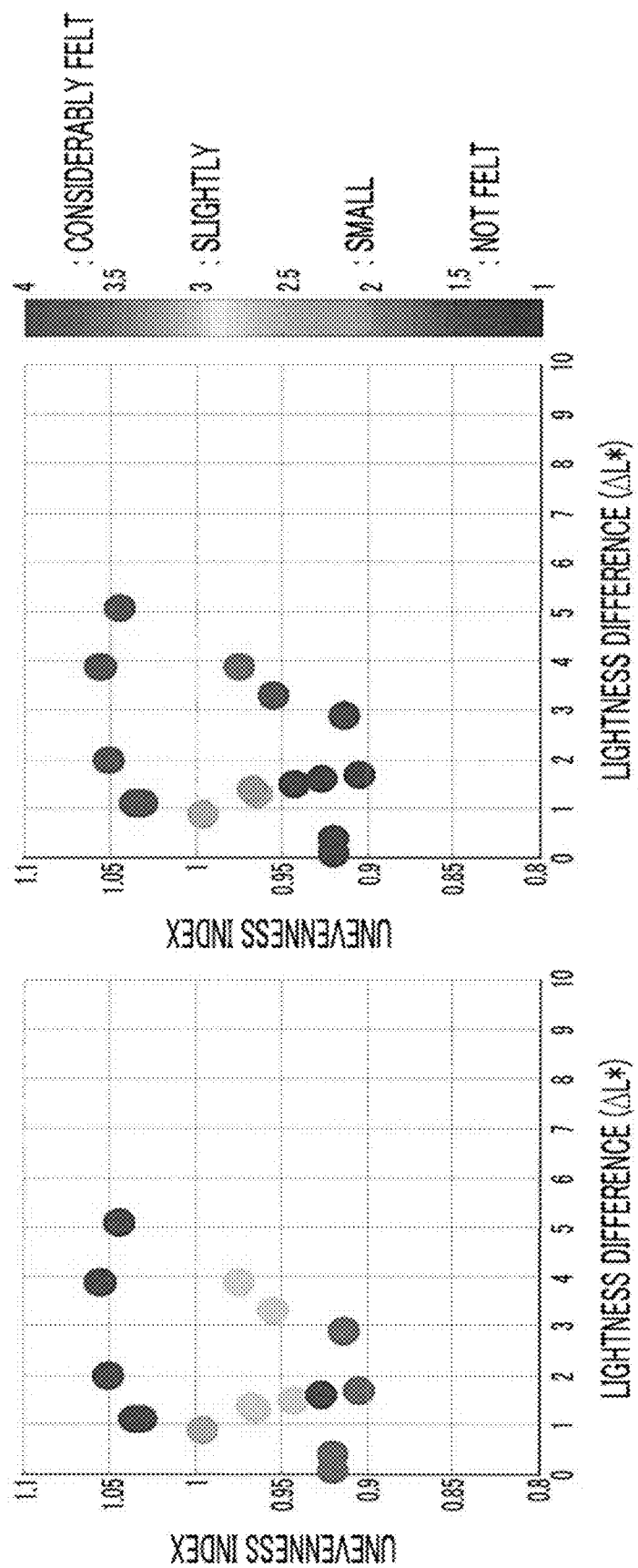

SKIN GLOSS EVALUATION DEVICE, SKIN GLOSS EVALUATION METHOD, AND SKIN GLOSS EVALUATION PROGRAM

CROSS-REFERENCE TO RELATED APPLICATIONS

This application is a Continuation of PCT International Application No. PCT/JP2016/071452 filed on Jul. 21, 2016, which claims priority under 35 U.S.C. § 119(a) to Japanese Patent Application No. 2015-178472 filed on Sep. 10, 2015. Each of the above application(s) is hereby expressly incorporated by reference, in its entirety, into the present application.

BACKGROUND OF THE INVENTION

1. Field of the Invention

The present invention relates to a gloss evaluation device, a gloss evaluation method, and a non-transitory computer readable recording medium storing gloss evaluation program, and more particularly to, a skin gloss evaluation device, a skin gloss evaluation method, and a non-transitory computer readable recording medium storing skin gloss evaluation program for evaluating gloss of skin by determining whether the gloss of the skin is luster or oiliness on the basis of a captured image obtained by imaging a face of a subject or quantifying intensity (degree) of the luster or the oiliness.

2. Description of the Related Art

Gloss of an object is an important factor for determining impression or texture of the object. In particular, since gloss of a skin is an index that affects texture of the skin, evaluation thereof is an important element in the development of foundation, skin care products, or the like in the field of beauty.

The gloss of the skin may be expressed as "luster" in which a reflectance of light is moderate and the skin looks visually beautiful, for example, in bare skin or makeup skin or may be expressed as "oiliness" in which the reflectance of light is high and the skin does not look visually beautiful. However, in recent years, various methods of evaluating such gloss of the skin, that is, luster or oiliness have been proposed.

For example, JP2014-046698A discloses a method of calculating the amount of oiliness of skin on the basis of a polarized image of the skin and evaluating intensity (degree) of the oiliness of the skin.

JP2002-017689A proposes a method of irradiating a face of a subject with diffused light from one direction, imaging the face of the subject at a plurality of light reception angles, and evaluating a degree of gloss of skin using a combination of an incident angle of an acquired polarized image and the light reception angle, and a brightness value (L* value) acquired by converting brightness of the polarized image in a multi-gradation.

JP2011-130808A discloses a method of acquiring a non-polarized image and a polarized image obtained by imaging skin, calculating, as a feature amount, a degree of divergence (skewness or kurtosis) between an average value of a subtraction result acquired by subtracting a pixel value of the non-polarized image from a pixel value of the polarized image and a normal distribution of a distribution of the subtraction result, and evaluating intensity (degree) of luster of skin of a subject on the basis of the feature amount.

JP2011-044132A discloses a method of specifying an oiliness component on the basis of values of chroma and lightness acquired from an image obtained by imaging skin and evaluating intensity (degree) of the oiliness.

SUMMARY OF THE INVENTION

However, in the evaluation methods of JP2014-046698A, JP2002-017689A, and JP2011-130808A, since it is necessary to acquire a polarized image, a device such as a polarization filter must be prepared, and the skin cannot be easily evaluated.

Further, in the evaluation method of JP2011-044132A, the oiliness of the skin can be detected, but the luster of the skin cannot be detected.

Further, in any of the evaluation methods of JP2014-046698A, JP2002-017689A, JP2011-130808A, and JP2011-044132A, the gloss of the skin cannot be evaluated, that is, whether the gloss of the skin is luster or oiliness cannot be specified. Further, there is another problem in that a degree of the specified luster or oiliness cannot be quantitatively evaluated.

The present invention has been made to solve such problems of the related art, and an object of the present invention is to provide a skin gloss evaluation device, a skin gloss evaluation method, and a non-transitory computer readable recording medium storing skin gloss evaluation program capable of easily evaluating gloss of the skin.

A skin gloss evaluation device according to the present invention comprises: an image input unit that inputs a captured image obtained by imaging a face of a subject; an analysis range setting unit that sets a portion in which it is easy for gloss of skin of the subject to occur and a portion in which it is difficult for gloss to occur in the captured image as analysis ranges; a skin evaluation index calculation unit that calculates a skin evaluation index related to the set analysis range; and a luster and oiliness evaluation unit that evaluates luster and oiliness of the face of the subject on the basis of the skin evaluation index, wherein the skin evaluation index calculation unit calculates, as the skin evaluation index, a chroma difference ($\Delta C^*$) between the portion in which it is easy for the gloss of the face of the subject to occur and the portion in which it is difficult for gloss to occur that are set as the analysis ranges, and the luster and oiliness evaluation unit classifies and evaluates luster and oiliness on the basis of the chroma difference ($\Delta C^*$).

Here, the skin evaluation index calculation unit can further calculate, as the skin evaluation index, a lightness difference ($\Delta L^*$) between the portion in which it is easy for the gloss of the face of the subject to occur and the portion in which it is difficult for gloss to occur that are set as the analysis ranges, and the luster and oiliness evaluation unit can classify and evaluate the luster and the oiliness on the basis of the chroma difference ($\Delta C^*$) and the lightness difference ($\Delta L^*$).

Further, the skin evaluation index calculation unit can convert an L* image of the portion in which it is easy for the gloss of the skin to occur that is set as the analysis range into information on a spatial frequency as the skin evaluation index, weight the information on the spatial frequency with visual frequency characteristics of human (visual transfer function (VTF); visual transfer function), and further calculate a total value of the weighted spatial frequency as an unevenness index, and the luster and oiliness evaluation unit can further evaluate intensity of luster or oiliness of the face of the subject on the basis of the unevenness index.

A skin gloss evaluation method according to the present invention comprises: inputting a captured image obtained by imaging a face of a subject; setting a portion in which it is easy for gloss of skin of the subject to occur and a portion in which it is difficult for gloss to occur in the captured image as analysis ranges; calculating a skin evaluation index related to the set analysis range; and evaluating luster and oiliness of the face of the subject on the basis of the skin evaluation index, wherein the skin gloss evaluation method further comprises: calculating, as the skin evaluation index, a chroma difference ($\Delta C^*$) between the portion in which it is easy for the gloss of the face of the subject to occur and the portion in which it is difficult for gloss to occur that are set as the analysis ranges, and classifying and evaluating luster and oiliness on the basis of the chroma difference ($\Delta C^*$).

Here, a lightness difference ($\Delta L^*$) between the portion in which it is easy for the gloss of the face of the subject to occur and the portion in which it is difficult for gloss to occur that are set as the analysis ranges can be further calculated, as the skin evaluation index, and the luster and the oiliness can be classified and evaluated on the basis of the chroma difference ($\Delta C^*$) and the lightness difference ($\Delta L^*$).

Further, an $L^*$ image of the portion in which it is easy for the gloss of the skin to occur that is set as the analysis range can be converted into information on a spatial frequency as the skin evaluation index, the information on the spatial frequency can be weighted with visual frequency characteristics of human (visual transfer function (VTF); visual transfer function), and a total value of the weighted spatial frequency can be further calculated as an unevenness index, and intensity of luster or oiliness of the face of the subject can be further evaluated on the basis of the unevenness index.

A non-transitory computer readable recording medium storing skin gloss evaluation program according to the present invention comprises: an image input step of inputting a captured image obtained by imaging a face of a subject; an analysis range setting step of setting a portion in which it is easy for gloss of skin of the subject to occur and a portion in which it is difficult for gloss to occur in the captured image as analysis ranges; a skin evaluation index calculation step of calculating a skin evaluation index related to the set analysis range; and a luster and oiliness evaluation step of evaluating luster and oiliness of the face of the subject on the basis of the skin evaluation index, wherein the skin evaluation index calculation step includes calculating, as the skin evaluation index, a chroma difference ($\Delta C^*$) between the portion in which it is easy for the gloss of the face of the subject to occur and the portion in which it is difficult for gloss to occur that are set as the analysis ranges, and the luster and oiliness evaluation step includes classifying and evaluating luster and oiliness on the basis of the chroma difference ($\Delta C^*$).

Here, the skin evaluation index calculation step can include further calculating, as the skin evaluation index, a lightness difference ($\Delta L^*$) between the portion in which it is easy for the gloss of the face of the subject to occur and the portion in which it is difficult for gloss to occur that are set as the analysis ranges, and the luster and oiliness evaluation step can include classifying and evaluating the luster and the oiliness on the basis of the chroma difference ($\Delta C^*$) and the lightness difference ($\Delta L^*$).

Further, the skin evaluation index calculation step can include converting an $L^*$ image of the portion in which it is easy for the gloss of the skin to occur that is set as the analysis range into information on a spatial frequency as the skin evaluation index, weighting the information on the spatial frequency with visual frequency characteristics of human (VTF visual transfer function), and calculating a total value of the weighted spatial frequency as an unevenness index, and the luster and oiliness evaluation step can include further evaluating intensity of luster and oiliness of the face of the subject on the basis of the unevenness index.

According to the present invention, it is possible to easily determine and evaluate whether the gloss of the skin is luster or oiliness. Further, it is possible to quantitatively evaluate intensity (degree) of the luster or oiliness of the specified skin.

BRIEF DESCRIPTION OF THE DRAWINGS

The patent or application file contains at least one drawing executed in color. Copies of this patent or patent application published with color drawing(s) will be provided by the Office upon request and payment of the necessary fee.

FIGS. 11A and 11B are diagrams illustrating graphs showing a correlation between a chroma difference ($\Delta C^*$) and a lightness difference ($\Delta L^*$) for luster and oiliness of skin of a face of a subject, and a correlation between this graph and a sensory evaluation value, in which FIG. 11A illustrates intensity (degree) of the luster of the skin, and FIG. 11B illustrates intensity (degree) of the oiliness of the skin.

FIGS. 12A and 12B are diagrams illustrating a relationship between an unevenness index, a lightness difference ($\Delta L^*$), and a sensory evaluation value for luster and oiliness of skin of a face of a subject, in which FIG. 12A illustrates a degree of the luster of the skin, and FIG. 12B illustrates a degree of the oiliness of the skin.

DESCRIPTION OF THE PREFERRED EMBODIMENTS

Hereinafter, embodiments of the present invention will be described with reference to the accompanying drawings.

Embodiment 1

Figure 1:
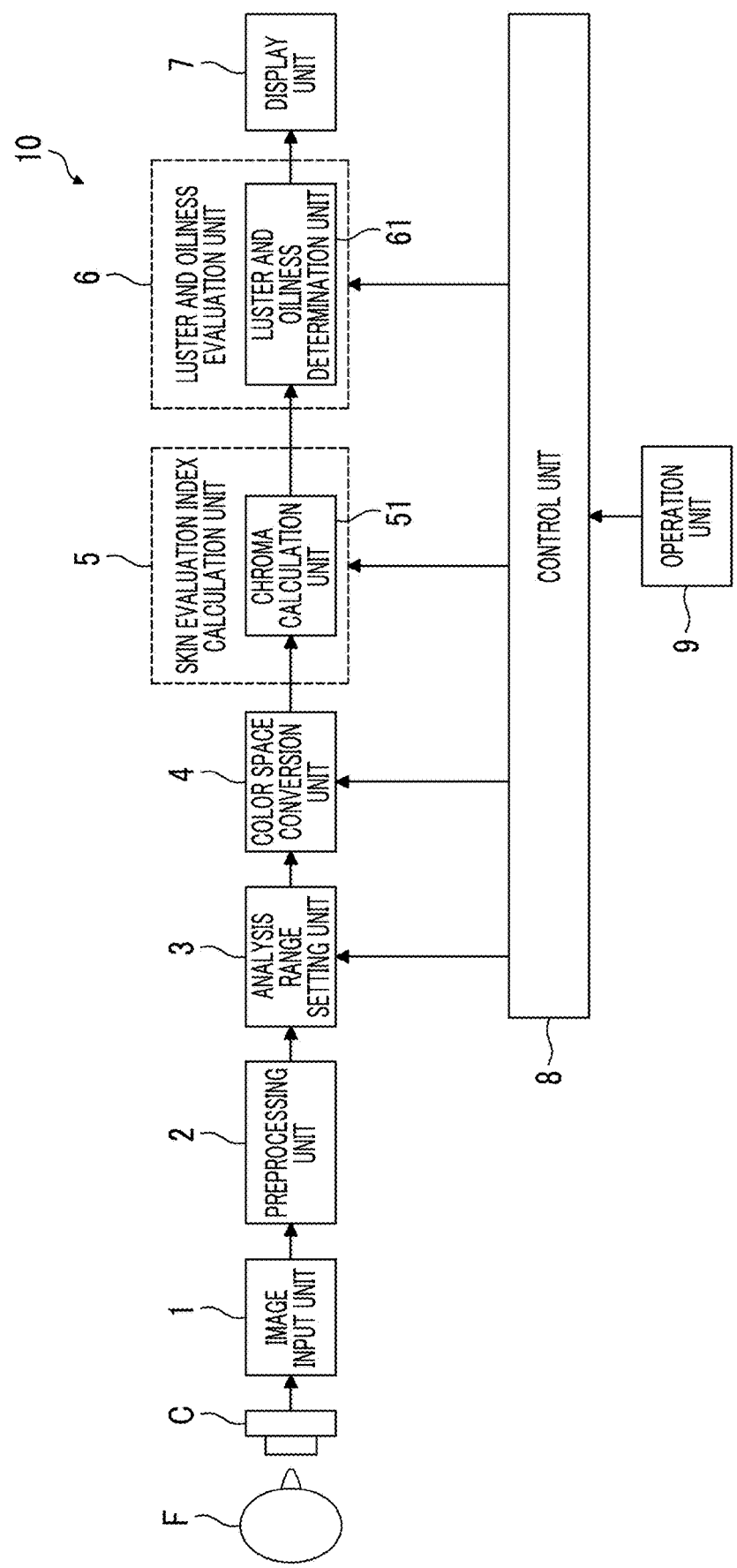
FIG. 1 is a block diagram illustrating a configuration of a skin gloss evaluation device according to Embodiment 1 of the present invention.

FIG. 1 illustrates a configuration of a skin gloss evaluation device according to Embodiment 1 of the present invention.

The skin gloss evaluation device evaluates gloss of skin of a face F of a subject using a captured image obtained by imaging the face F of the subject using a camera C, and includes an image input unit 1 connected to the camera C. A preprocessing unit 2, an analysis range setting unit 3, a color space conversion unit 4, a skin evaluation index calculation unit 5, a luster and oiliness evaluation unit 6, and a display unit 7 are sequentially connected to the image input unit 1. Further, a control unit 8 is connected to the analysis range setting unit 3, the color space conversion unit 4, the skin evaluation index calculation unit 5, and the luster and oiliness evaluation unit 6. An operation unit 9 is connected to the control unit 8.

The image input unit 1 receives a captured image from the camera C which has imaged the face F of the subject. Here, it is assumed that the captured image input from the camera C has an RGB color space (Red, Green, Blue color space). The face F of the subject may be bare skin or makeup skin. The camera C may be any camera as long as the camera can image the face F of the subject. A digital camera, a charge coupled device (CCD) camera, or the like can be used as the camera C. For example, a captured image captured by a smart device (a mobile phone such as a smartphone, or a tablet PC) can also be used. Further, an image obtained by imaging a replica or an image obtained by optical simulation (for example, a Monte Carlo method or a photon mapping method in ray tracing) may be input. Further, a captured image obtained by cutting out a part of a face image may be input. Further, for example, a face image imaging device VISIA™ manufactured by Canfield Scientific can be used. An imaging condition is not particularly limited, but it is preferable to irradiate the face F of the subject with light from a front obliquely upward side of the face F of the subject so that it is easy for gloss to occur on the skin.

The preprocessing unit 2 performs preprocessing such as light amount correction and noise removal on the captured image that is input from the image input unit 1.

The analysis range setting unit 3 sets an evaluation region R1 at a place at which it is easy for gloss to occur in the face F of the subject with respect to the captured image input from the preprocessing unit 2, and sets a reference region R1a at a place at which it is difficult for the gloss to occur. Specifically, examples of a place at which it is easy for the gloss to occur may include a forehead, a cheekbone, and an eyelid in a case where a light source is radiated from an upper side or an obliquely upward side of the face. It is preferable for the evaluation region R1 to be set in the cheekbone among them. Examples of a place at which it is difficult for the gloss to occur include a portion below an eye, a mouth corner, a portion near an outline.

Figure 2:
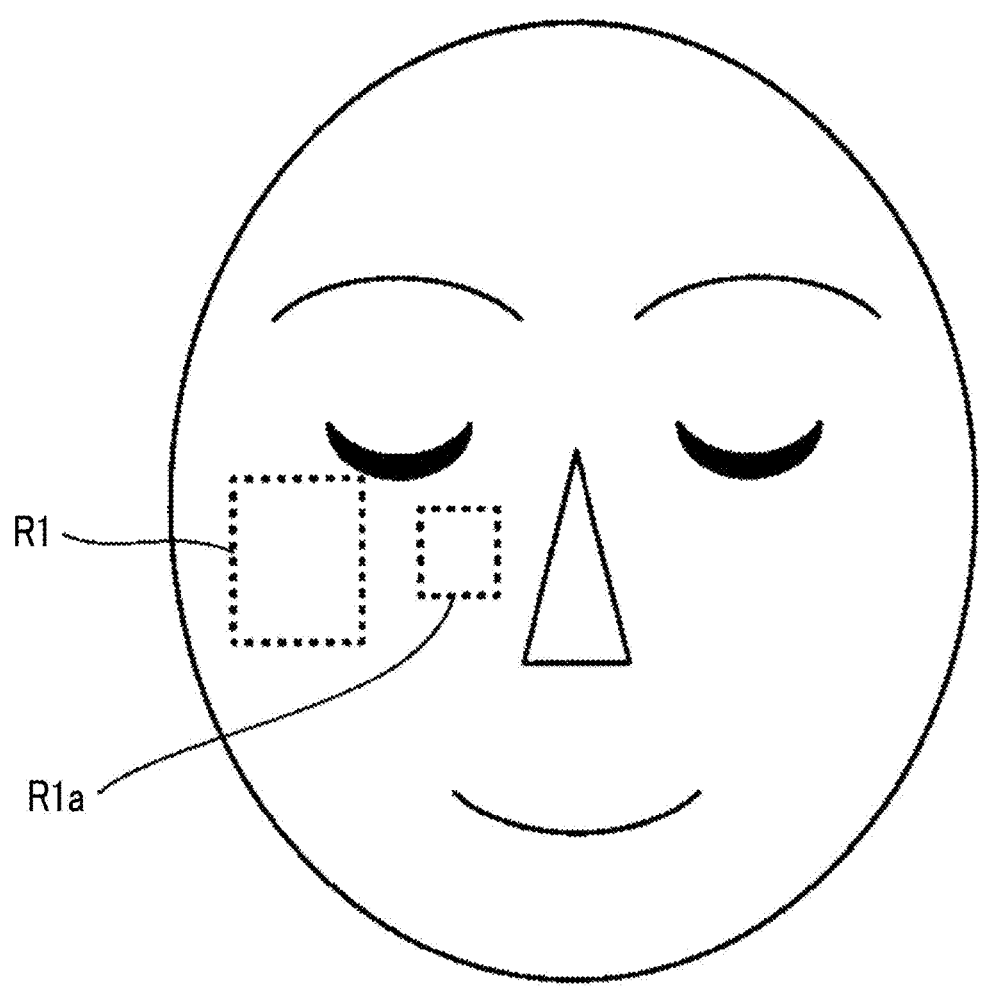
FIG. 2 is a diagram illustrating an evaluation region set in a face of a subject.

In this embodiment, as illustrated in FIG. 2, the evaluation region R1 is set in the cheekbone, and the reference region R1a is set in a portion near a nose and below an eye.

The color space conversion unit 4 converts the color space of portions of the evaluation region R1 and the reference region R1a of the captured image input from the analysis range setting unit 3 to generate a CIE L*a*b* color space converted image (an image converted into a value of an L*a*b* color space defined by Commission internationale de l'eclairage. Hereinafter, the CIE L*a*b* color space is simply referred to as an L*a*b* color space). In a case where the color space is converted into the L*a*b* color space, for example, a D65 light source can be used as a calculation light source. The color space conversion unit 4 separates the generated color space converted image into a lightness component (brightness component) and a color component to generate a lightness component image and a color component image. Specifically, in a case where color space converted image has an L*a*b* color space, the lightness component indicates an L* component, and the color component indicates a C* component (chroma component, $C^* = \{(a^*)^2 + (b^*)^2\}^{1/2}$).

The skin evaluation index calculation unit 5 includes a chroma calculation unit 51 connected to the color space conversion unit 4. The chroma calculation unit 51 receives the color space converted image obtained by converting the color space of the portion of the evaluation region R1 and the reference region R1a from the color space conversion unit 4, and calculates a skin evaluation index on the basis of the chroma component of the evaluation region R1 and the chroma component of the reference region R1a. The skin evaluation index calculation unit 5 outputs the skin evaluation index calculated by the chroma calculation unit 51 to the luster and oiliness evaluation unit 6.

The luster and oiliness evaluation unit 6 includes a luster and oiliness determination unit 61 that is connected to the chroma calculation unit 51 of the skin evaluation index calculation unit 5. On the basis of the skin evaluation index calculated by the chroma calculation unit 51, the luster and oiliness determination unit 61 classifies and evaluates the gloss of the skin of the face F of the subject, that is, determines whether the gloss of the skin of the subject F is luster or oiliness, and outputs a result thereof to the display unit 7.

The display unit 7 includes, for example, a display device such as a liquid crystal display (LCD), and displays a result of the evaluation of luster and oiliness in the luster and oiliness evaluation unit 6.

The operation unit 9 allows an operator to perform an information input operation, and can be formed from a keyboard, a mouse, a trackball, a touch panel, or the like.

The control unit 8 performs control of each unit in the skin gloss evaluation device on the basis of, for example, various command signals input from the operation unit 9 by the operator.

The analysis range setting unit 3, the color space conversion unit 4, the skin evaluation index calculation unit 5, the luster and oiliness evaluation unit 6, and the control unit 8 are configured of a central processing unit (CPU), and an operation program for causing the CPU to perform various processes, but may be configured of a digital circuit. Further, a memory can be connected to the CPU via a signal line such as a bus. For example, the color space converted image generated by the color space conversion unit 4, the image generated by the skin evaluation index calculation unit 5, and the evaluation result of the luster or oiliness calculated by the luster and oiliness evaluation unit 6 can be stored in the memory, and the images and the evaluation result of the luster or oiliness stored in the memory can be displayed on the display unit 7 under the control of the control unit 8.

Further, a database that has stored a relationship between the sensory evaluation value calculated by performing the sensory evaluation of the luster or oiliness of the skin in advance and the skin evaluation index can also be connected to the luster and oiliness evaluation unit 6. The luster and oiliness evaluation unit 6 can evaluate the gloss of the skin by comparing the relationship between the sensory evaluation value read from the database and the skin evaluation index with the skin evaluation index input from the skin evaluation index calculation unit 5.

Next, the chroma calculation unit 51 of the skin evaluation index calculation unit 5 will be described in detail.

The chroma calculation unit 51 receives the color space converted image obtained by converting the color space of the portion of the evaluation region R1 and the reference region R1a from the color space conversion unit 4, and calculates a difference between an average value of the chroma component (C* component) of the evaluation region R1 in which it is easy for gloss to occur, which is set as an analysis range, and an average value of the chroma component (C* component) of the reference region R1a in which it is difficult for gloss to occur, that is, a chroma difference (ΔC*) as the skin evaluation index.

Next, the luster and oiliness determination unit 61 of the luster and oiliness evaluation unit 6 will be described in detail.

The luster and oiliness determination unit 61 determines that the gloss occurring on the skin is "oiliness" in a case where the ΔC* calculated as the skin evaluation index in the chroma calculation unit 51 is greater than a preset threshold value, and determines that the gloss generated on the skin is "luster" in a case where ΔC* is equal to or smaller than the threshold value.

Specifically, for example, the threshold value is set to ΔC*=−2.3, and the luster and oiliness determination unit 61 determines that the gloss generated on the skin is "gloss" in a case where ΔC* is greater than −2.3, and determines that the gloss generated on the skin is "oiliness" in a case where ΔC* is equal to or smaller than −2.3. The threshold value may be set, for example, in a range of −2.3±0.5, and may be appropriately set according to imaging conditions or the like.

Further, as in this embodiment, the determination is not limited to the determination for clearly distinguishing "luster" and "oiliness" from each other using one preset threshold value, and a numerical range in which both "luster and oiliness" are felt can also be set. Specifically, a threshold value for determining the gloss occurring on the skin to be "luster", a threshold value for determining the gloss occurring on the skin to be "oiliness", and a numerical range between the threshold values, that is, a range for determining that both "luster" and "oiliness" are felt in a case where ΔC* exists between the two threshold values can also be set.

Such a threshold value or a predetermined range can be set from the relationship between the sensory evaluation value calculated by performing sensory evaluation of the luster and the oiliness of the skin in advance and the skin evaluation index, that is, a correspondence relationship between a visual evaluation value of the intensity (degree) of the luster or the oiliness acquired from the image in advance and the calculated ΔC*.

Next, an operation according to Embodiment 1 will be described.

Figure 3:
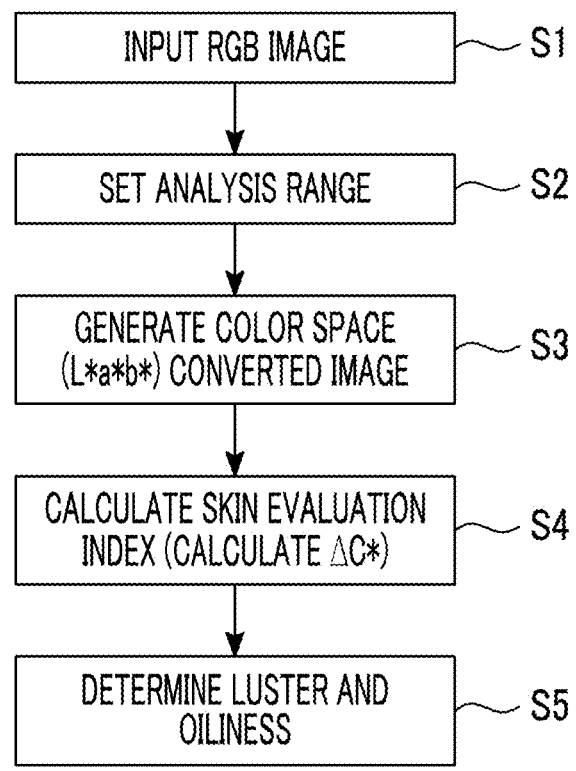
FIG. 3 is a diagram illustrating a skin gloss evaluation method according to Embodiment 1.

FIG. 3 is a diagram illustrating a flowchart of a skin gloss evaluation method that is executed by the skin gloss evaluation device according to Embodiment 1.

First, an RGB image obtained by imaging the face F of the subject using the camera C is input from the camera C to the preprocessing unit 2 via the image input unit 1 of the skin gloss evaluation device as illustrated in FIG. 1 (step S1). The captured image is subjected to preprocessing such as light source correction and noise removal and then output from the preprocessing unit 2 to the analysis range setting unit 3. The evaluation region R1 is set as the analysis range in a region in which it is easy for the gloss of the skin to occur, and the reference region R1a is set as the analysis range in a region in which it is difficult for the gloss to occur (step S2). The captured image in which the analysis ranges have been set is output to the color space conversion unit 4, and color spaces of the evaluation region R1 and the reference region R1a of the captured image are converted into an L*a*b* color space by the color space conversion unit 4, and a color space converted image is generated. The color space conversion unit 4 extracts a chroma component (C* component) from the color space converted image and generates a chroma component image (C* component image) (step S3). The color space conversion unit 4 outputs the generated C* component image to the chroma calculation unit 51 of the skin evaluation index calculation unit 5.

The chroma calculation unit 51 can obtain the average value of the intensity of the C* component with respect to the evaluation region R1 set in the C* component image, and obtain the average value of the intensity of the C* component with respect to the reference region R1a set in the C* component image. Accordingly, it is possible to obtain the value of the overall C* component for the evaluation region R1 and the reference region R1a set in the face F of the subject. Subsequently, the chroma calculation unit 51 calculates a difference between the average value of the C* component in the evaluation region R1 and the average value of the C* component in the reference region R1a, that is, the chroma difference (ΔC*) as a skin evaluation index for evaluating the gloss of the skin (step S4) and outputs the skin evaluation index to the luster and oiliness determination unit 61 of the luster and oiliness evaluation unit 6.

The luster and oiliness determination unit 61 classifies and evaluates the gloss of the skin on the basis of the input difference between the average value of the C* component in the evaluation region R1 and the average value of the C* component in the reference region R1a, that is, the chroma difference (ΔC*), and a preset threshold value (step S5).

Embodiment 2

In Embodiment 1, the classification and the evaluation of the gloss of the skin has been performed using only the chroma difference (ΔC*) calculated by the chroma calculation unit 51 of the skin evaluation index calculation unit 5, but the present invention is not limited thereto, and the skin evaluation index calculation unit 5 can also calculate the lightness difference (ΔL*) and perform classification and evaluation on the gloss of the skin using the chroma difference and the lightness difference.

Figure 4:
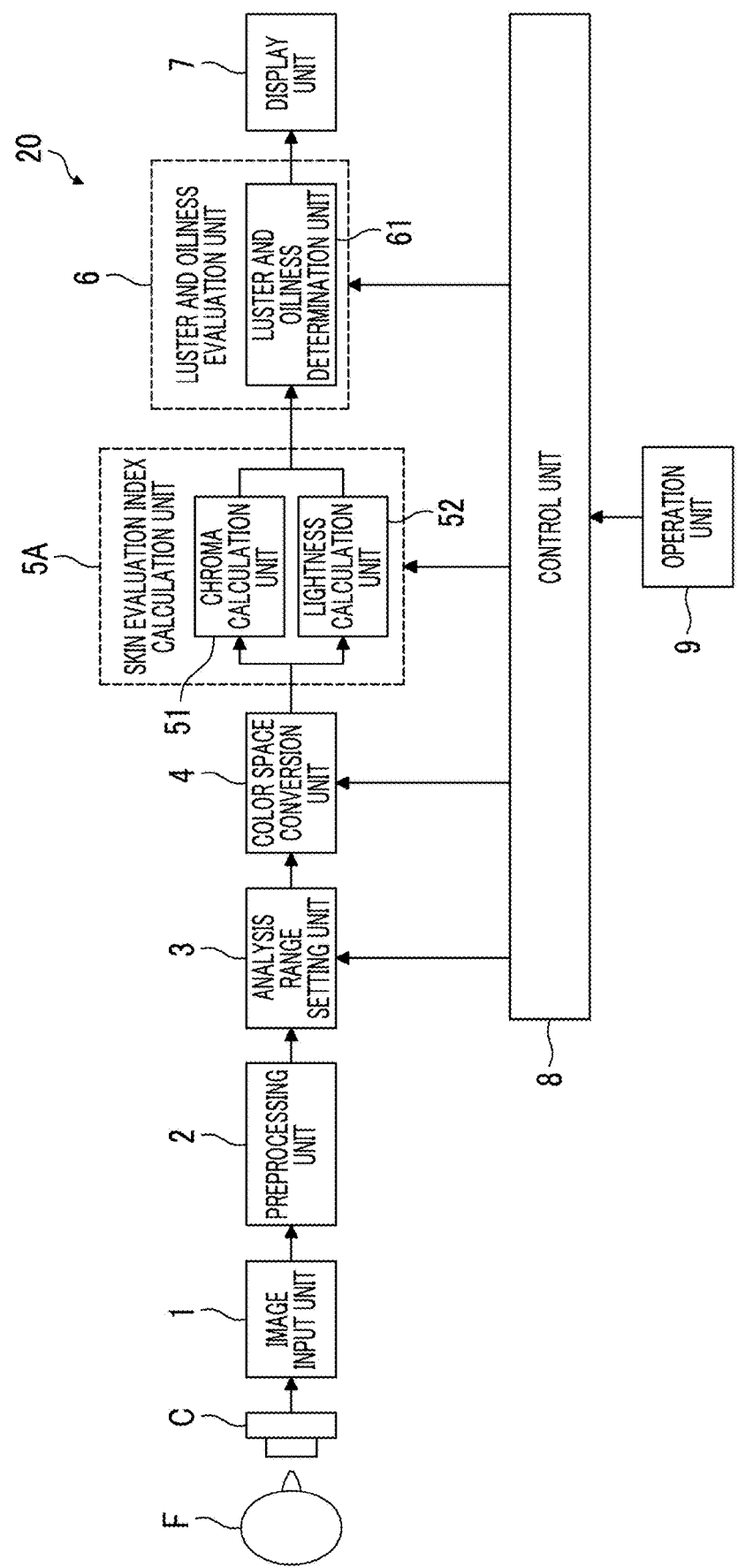
FIG. 4 is a block diagram illustrating a configuration of a skin gloss evaluation device according to Embodiment 2 of the present invention.

FIG. 4 illustrates a configuration of the skin gloss evaluation device according to Embodiment 2. This skin gloss evaluation device 20 includes a skin evaluation index calculation unit 5A including the chroma calculation unit 51 and a lightness calculation unit 52 instead of the skin evaluation index calculation unit 5 including only the chroma calculation unit 51 in the skin gloss evaluation device 10 according to Embodiment 1 illustrated in FIG. 1. That is, in Embodiment 2, a configuration other than the skin evaluation index calculation unit 5 illustrated in FIG. 1 is the same configuration as the skin gloss evaluation device 10 according to Embodiment 1.

The skin evaluation index calculation unit 5A includes a chroma calculation unit 51 and a lightness calculation unit 52 that are connected to the color space conversion unit 4.

The chroma calculation unit 51 receives the color space converted image obtained by converting the color space of the portion of the evaluation region R1 and the reference region R1a from the color space conversion unit 4, and calculates a difference between an average value of the chroma component (C* component) of the evaluation region R1 in which it is easy for gloss to occur, which is set as an analysis range, and an average value of the chroma component (C* component) of the reference region R1a in which it is difficult for gloss to occur, that is, a chroma difference ($\Delta C^*$) as the skin evaluation index, similar to Embodiment 1.

The lightness calculation unit 52 receives the color space converted image obtained by converting the color space of the portion of the evaluation region R1 and the reference region R1a from the color space conversion unit 4, and calculates a difference ($\Delta L^*$) between an average value of the lightness component ($L^*$ component) of the evaluation region R1 in which it is easy for gloss to occur, which is set as an analysis range, and an average value of the lightness component ($L^*$ component) of the reference region R1a in which it is difficult for gloss to occur, as the skin evaluation index.

The skin evaluation index calculation unit 5A outputs a difference ($\Delta L^*$) in an average value of a lightness component between the evaluation region R1 and the reference region R1a, and a difference in an average value of the chroma component, that is, a chroma difference ($\Delta C^*$) to the luster and oiliness specifying unit 61 as skin evaluation indexes.

On the basis of the skin evaluation indexes ($\Delta C^*$ and $\Delta L^*$) calculated by the chroma calculation unit 51 and the lightness calculation unit 52, the luster and oiliness determination unit 61 evaluates the gloss of the skin of the face F of the subject, that is, determines whether the gloss of the skin of the subject F is luster or oiliness.

Here, a relationship (a threshold value, a discriminant function, or the like) between the sensory evaluation value calculated by performing sensory evaluation of the luster and oiliness of the skin and the skin evaluation index ($\Delta C^*$ and $\Delta L^*$) is obtained in advance, and the relationship between the sensory evaluation value and the skin evaluation index obtained in advance is compared with the skin evaluation index input from the skin evaluation index calculation unit 5 to classify and evaluate the luster and oiliness. The calculated relationship between the sensory evaluation value and the skin evaluation index can be obtained through Fisher's linear discriminant analysis, pattern recognition using Support Vector Machine (SVM), or the like.

Next, an operation according to Embodiment 2 will be described.

Figure 5:
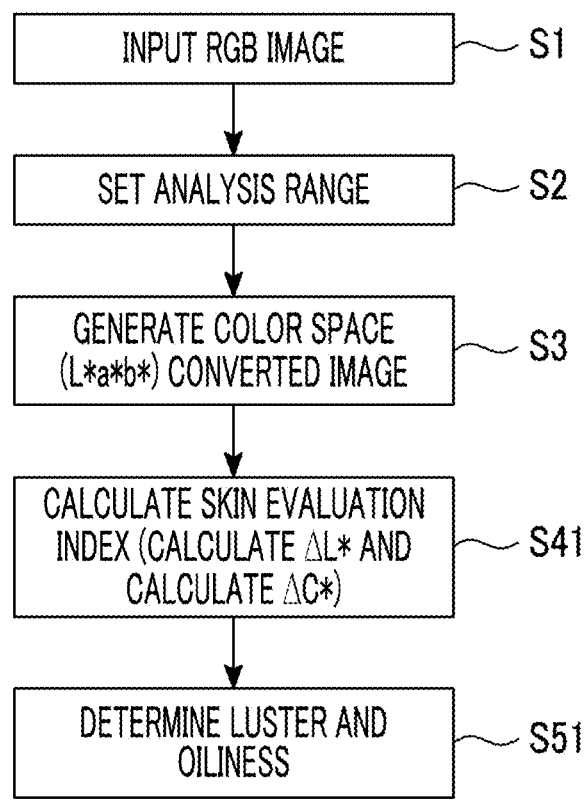
FIG. 5 is a diagram illustrating a skin gloss evaluation method according to Embodiment 2.

FIG. 5 is a diagram illustrating a flowchart of a skin gloss evaluation method that is executed by the skin gloss evaluation device according to Embodiment 2. This flowchart is a flowchart in which steps S41 and S51 are executed instead of steps S4 and S5 in the flowchart of the skin gloss evaluation method that is executed by the skin gloss evaluation device according to Embodiment 1 illustrated in FIG. 3.

In the skin evaluation index calculation unit 5A, the chroma calculation unit 51 obtains the average value of the intensity of the $C^*$ component with respect to the evaluation region R1 set in the $C^*$ component image, obtains the average value of the intensity of the $C^*$ component with respect to the reference region R1a set in the $C^*$ component image, calculates a difference between the average value of the $C^*$ component in the evaluation region R1 and the average value of the $C^*$ component in the reference region R1a, that is, the chroma difference ($\Delta C^*$) as the skin evaluation index (step S41), and outputs the chroma difference ($\Delta C^*$) to the luster and oiliness determination unit 61 of the luster and oiliness evaluation unit 6.

Further, the lightness calculation unit 52 obtains the average value of the intensity of the $L^*$ component with respect to the evaluation region R1 set in the $L^*$ image, obtains the average value of the intensity of the $L^*$ component with respect to the reference region R1a set in the $L^*$ image, calculates a difference between the average value of the $L^*$ component in the evaluation region R1 and the average value of the $L^*$ component in the reference region R1a, that is, the lightness difference ($\Delta L^*$) as the skin evaluation index (step S41), and outputs the lightness difference ($\Delta L^*$) to the luster and oiliness determination unit 61 of the luster and oiliness evaluation unit 6.

The luster and oiliness determination unit 61 evaluates the gloss of the skin of the face F of the subject on the basis of the skin evaluation indexes ($\Delta C^*$ and $\Delta L^*$) calculated by the chroma calculation unit 51 and the lightness calculation unit 52.

The relationship between the sensory evaluation value calculated by performing the sensory evaluation on the luster and oiliness of the skin on the skin in advance and the skin evaluation index ($\Delta C^*$ and $\Delta L^*$) is compared with the skin evaluation index ($\Delta C^*$ and $\Delta L^*$) input from the skin evaluation index calculation unit 5 to evaluate the luster and the oiliness (step S51).

Embodiment 3

In Embodiment 1, the chroma difference ($\Delta C^*$) has been calculated, and the evaluation has been performed to determine whether the gloss of the skin is luster or oiliness on the basis of this chroma difference, but the present invention is not limited thereto. Further, the unevenness index can be calculated, the evaluation can first be performed to determine whether the gloss of the skin is luster or oiliness on the basis of the chroma difference ($\Delta C^*$), and then, the determined luster and oiliness can be quantitatively evaluated on the basis of the unevenness index.

Figure 6:
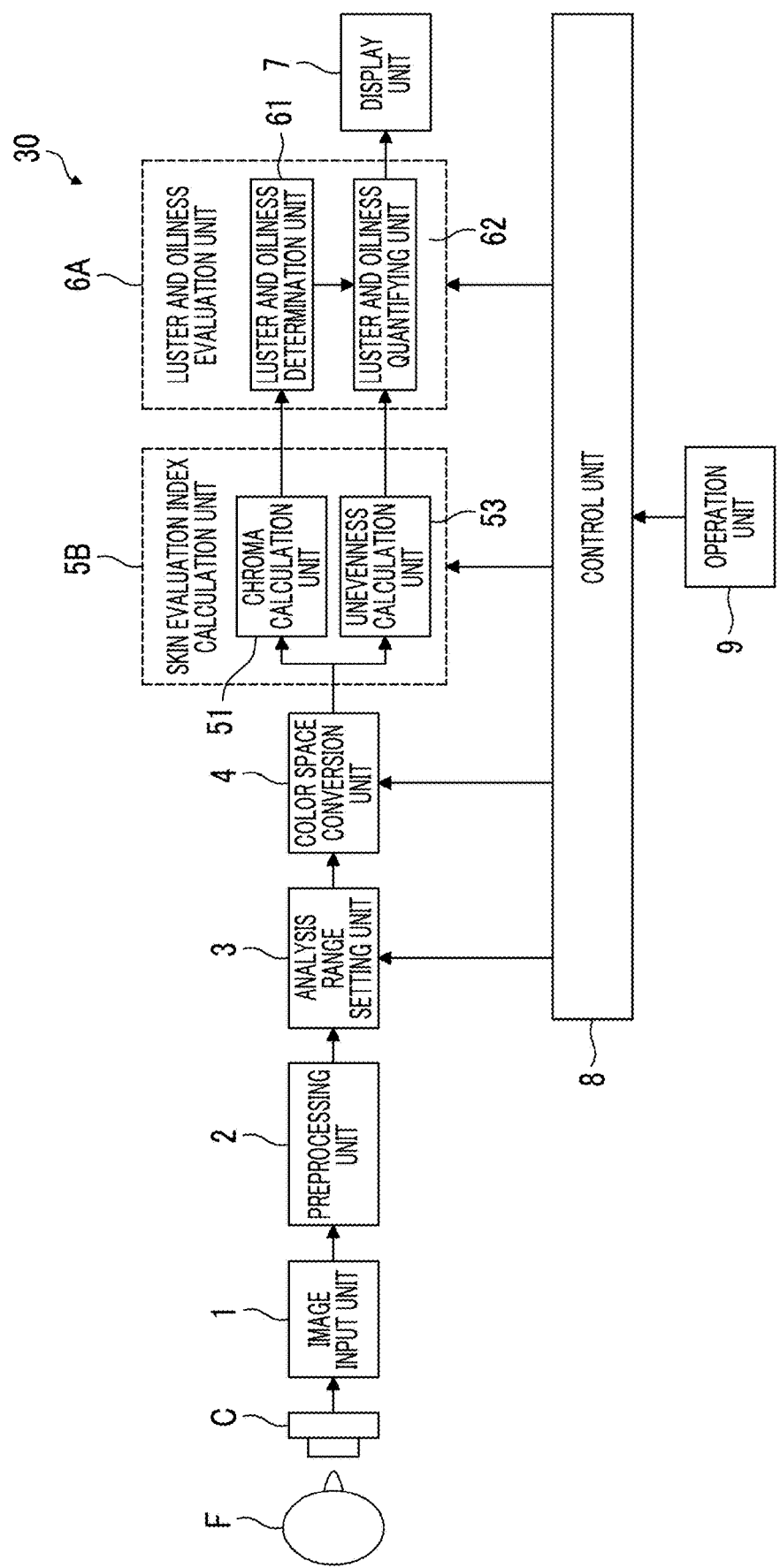
FIG. 6 is a block diagram illustrating a configuration of a skin gloss evaluation device according to Embodiment 3 of the present invention.

FIG. 6 illustrates a configuration of the skin gloss evaluation device according to Embodiment 3. The skin gloss evaluation device 30 includes a skin evaluation index calculation unit 5B including a chroma calculation unit 51 and an unevenness calculation unit 53, and a luster and oiliness evaluation unit 6A including a luster and oiliness determination unit 61 and a luster and oiliness quantifying unit 62, instead of the skin evaluation index calculation unit 5 including only the chroma calculation unit 51 and the luster and oiliness evaluation unit 6 including only the luster and oiliness determination unit 61 in the skin gloss evaluation device 10 according to Embodiment 1 illustrated in FIG. 1. That is, in Embodiment 3, the configuration is the same configuration as the skin gloss evaluation device 10 according to Embodiment 1 except for the skin evaluation index calculation unit 5 and the luster and oiliness evaluation unit 6 illustrated in FIG. 1.

The skin evaluation index calculation unit 5B includes a chroma calculation unit 51 and an unevenness calculation unit 53 that are connected to the color space conversion unit 4.

The chroma calculation unit 51 receives the color space converted image obtained by converting the color space of the portion of the evaluation region R1 and the reference region R1a from the color space conversion unit 4, and calculates a difference between an average value of the chroma component ($C^*$ component) of the evaluation region R1 in which it is easy for gloss to occur, which is set as an analysis range, and an average value of the chroma component ($C^*$ component) of the reference region R1a in which it is difficult for gloss to occur, that is, a chroma difference ($\Delta C^*$) as the skin evaluation index, similar to Embodiment 1.

The unevenness calculation unit 53 receives the L* image having the value of the L* component of the color space converted image from the color space conversion unit 4, performs a two-dimensional discrete Fourier transform process on the image to convert the image into information on a spatial frequency (for example, Winner Spectrum), weights this information on the spatial frequency with a parameter of visual frequency characteristics of human, and calculates a total value of the weighted spatial frequency as an unevenness index. Here, the visual frequency characteristics of the human refer to a visual transfer function (VTF; visual transfer characteristics) regarding a lightness variation. An observation distance was 30 cm using an approximation equation of Dooley shown in Equations (I) and (II) below in the VTF.

$$VTF = 5.05e^{-0.138u}(1 - e^{0.1u}). \quad \text{Equation (I)}$$

$$u = \frac{\pi l f_r}{180} \text{[cycles/deg]}. \quad \text{Equation (II)}$$

Here, l is the observation distance [mm], and $f_r$ is the spatial frequency [cycles/mm].

The skin evaluation index calculation unit 5B outputs the chroma difference ($\Delta C^*$) calculated by the chroma calculation unit 51 to the luster and oiliness determination unit 61 of the luster and oiliness evaluation unit 6A, and outputs the unevenness index calculated by the unevenness calculation unit 53 to the luster and oiliness quantifying unit 62.

The luster and oiliness evaluation unit 6A includes the luster and oiliness determination unit 61 and a luster and oiliness quantifying unit 62.

Similar to Embodiment 1, on the basis of the chroma difference ($\Delta C^*$) calculated by the chroma calculation unit 51, the luster and oiliness determination unit 61 evaluates the gloss of the skin of the face F of the subject, that is, determines whether the gloss of the skin of the subject F is luster or oiliness. Subsequently, the luster and oiliness determination unit 61 outputs a result of the determination to the luster and oiliness quantifying unit 62.

The luster and oiliness quantifying unit 62 quantitatively evaluates the intensity (degree) of the luster or the oiliness of the gloss of the skin determined by the luster and oiliness determination unit 61 on the basis of the unevenness index calculated by the unevenness calculation unit 53 of the skin evaluation index calculation unit 5B.

Here, the intensity of the luster and the oiliness is quantitatively evaluated by obtaining a relationship (threshold value or the like) between the sensory evaluation value calculated by performing sensory evaluation on the luster and the oiliness of the skin with various intensities (degrees) and the skin evaluation index (unevenness index) in advance, and comparing the relationship between the sensory evaluation value obtained in advance and the skin evaluation index with the skin evaluation index input from the skin evaluation index calculation unit 5B.

Next, an operation according to Embodiment 3 will be described.

Figure 7:
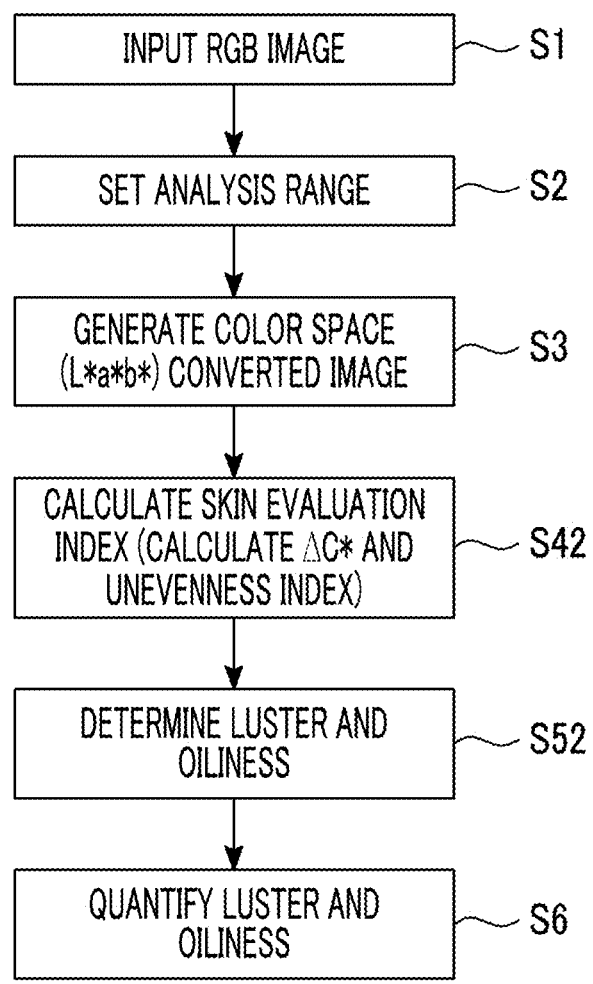
FIG. 7 is a diagram illustrating a skin gloss evaluation method according to Embodiment 3.

FIG. 7 is a diagram illustrating a flowchart of a skin gloss evaluation method that is executed by the skin gloss evaluation device according to Embodiment 3. This flowchart is a flowchart in which steps S42 and S52 are executed instead of steps S4 and S5 in the flowchart of the skin gloss evaluation method that is executed by the skin gloss evaluation device, and step S6 is executed according to Embodiment 1 illustrated in FIG. 3.

In the skin evaluation index calculation unit 5B, the chroma calculation unit 51 obtains the average value of the intensity of the C* component with respect to the evaluation region R1 set in the C* component image, obtains the average value of the intensity of the C* component with respect to the reference region R1a set in the C* component image, and calculates a difference between the average value of the C* component in the evaluation region R1 and the average value of the C* component in the reference region R1a, that is, the chroma difference ($\Delta C^*$), and the unevenness calculation unit 53 performs a two-dimensional discrete Fourier transform process on the L* image to convert the L* image into information on a spatial frequency (for example, Winner Spectrum), weights this information on the spatial frequency with a parameter of visual frequency characteristics of human, and calculates a total value of the weighted spatial frequency as an unevenness index (step S42). Subsequently, the chroma difference ($\Delta C^*$) is output to the luster and oiliness determination unit 61, and the unevenness index is output to the luster and oiliness quantifying unit 62.

The luster and oiliness determination unit 61 of the luster and oiliness evaluation unit 6A evaluates whether the gloss of the skin of the face F of the subject is luster or oiliness on the basis of the input chroma difference ($\Delta C^*$) (step S52), and outputs a result of the determination to the luster and oiliness quantifying unit 62.

The luster and oiliness quantifying unit 62 evaluates the intensity (degree) of the luster and the oiliness determined by the luster and oiliness determination unit 61 on the basis of the input unevenness index (step S6).

Modification Example of Embodiment 3

In Embodiment 3, the evaluation has been performed on the basis of only the chroma difference ($\Delta C^*$) to determine whether the gloss of the skin is luster or oiliness, but the present invention is not limited thereto. Further, the lightness difference ($\Delta L^*$) can be calculated, the evaluation can be performed to determine whether the gloss of the skin is luster or oiliness on the basis of the chroma difference and the lightness difference, and then, the determined luster and oiliness can also be quantitatively evaluated on the basis of the unevenness index.

Figure 8:
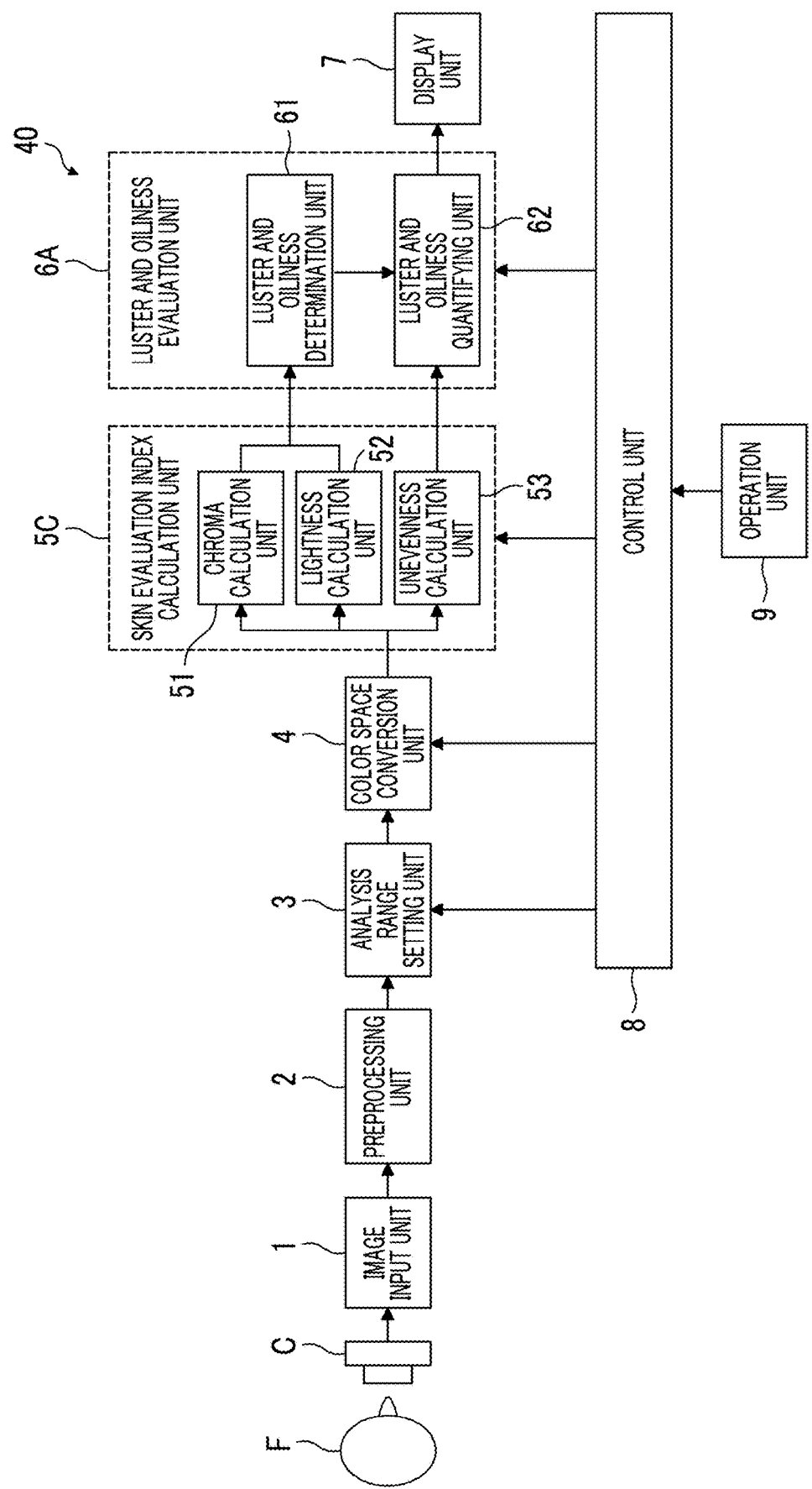
FIG. 8 is a diagram illustrating a modification example of the skin gloss evaluation device according to Embodiment 3.

FIG. 8 illustrates a configuration of the gloss evaluation device according to a modification example of Embodiment 3. A skin gloss evaluation device 40 includes a skin evaluation index calculation unit 5C including a chroma calculation unit 51, a lightness calculation unit 52, and an unevenness calculation unit 53, instead of the skin evaluation index calculation unit 5B including the chroma calculation unit 51 and the unevenness calculation unit 53 in the skin gloss evaluation device 30 according to Embodiment 3 illustrated in FIG. 6. That is, in the modification example of Embodiment 3, a configuration other than the skin evaluation index calculation unit 5B illustrated in FIG. 6 has the same configuration as the gloss evaluation device 30 of Embodiment 3.

The lightness calculation unit 52 included in the gloss evaluation device 40 of this embodiment has the same configuration and operation as those of the lightness calculation unit 52 of Embodiment 2.

Figure 9:
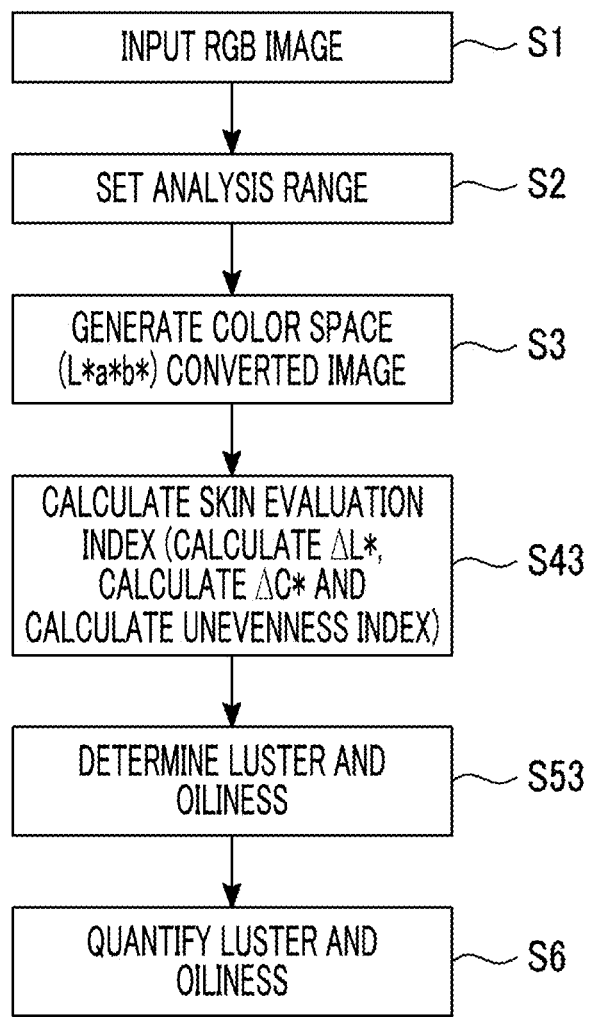
FIG. 9 is a diagram illustrating a modification example of the skin gloss evaluation method according to Embodiment 3.

FIG. 9 is a diagram illustrating a flowchart of a skin gloss evaluation method that is executed by the skin gloss evaluation device 40 according to the modification example of Embodiment 3. This flowchart is a flowchart in which steps S43 and S53 are executed instead of steps S42 and S52 of the flowchart of the skin gloss evaluation method that is executed by the skin gloss evaluation device according to Embodiment 3 illustrated in FIG. 7.

The modification example is the same as Embodiment 3 except that the skin evaluation index calculation unit 5C calculates the lightness difference, the chroma difference, and the unevenness index (step S43), and the luster and oiliness determination unit 61 of the luster and oiliness evaluation unit 6A specifies the gloss of the skin on the basis of the lightness difference and the chroma difference (step S53).

Figure 10:
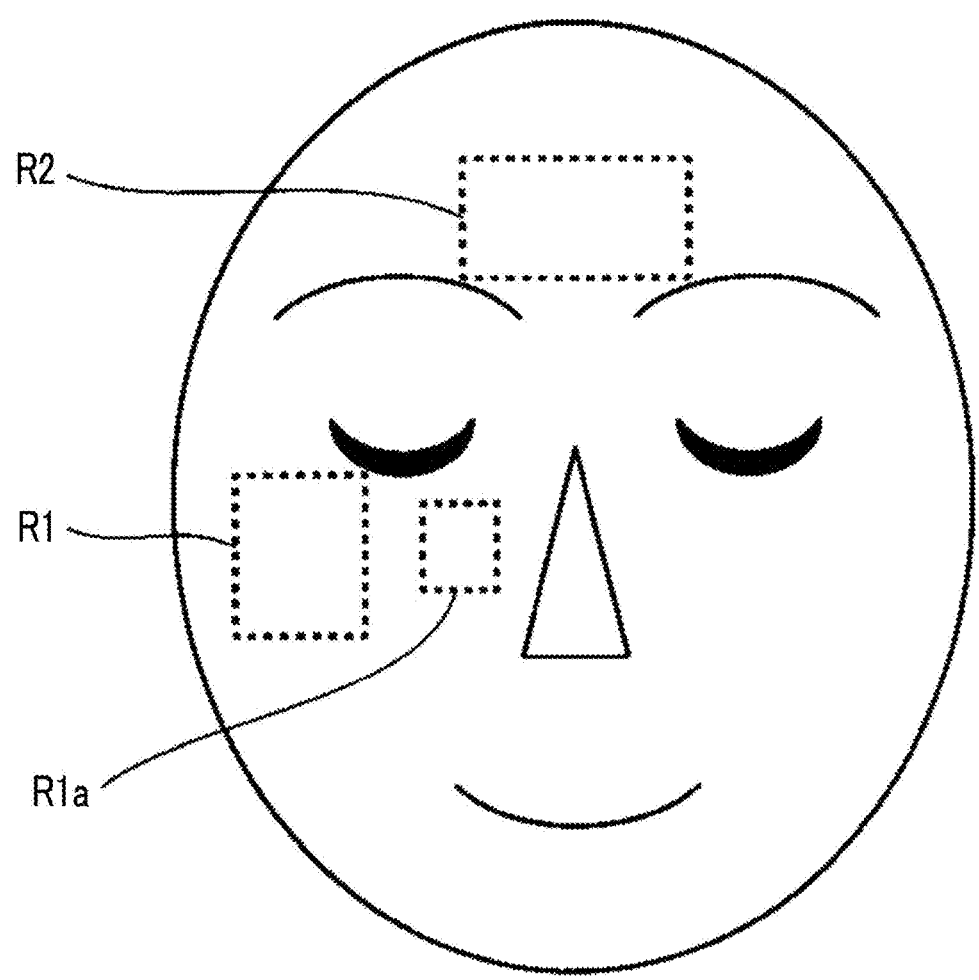
FIG. 10 is a diagram illustrating a modification example of an evaluation region set in a face of a subject.

In a case where the analysis range setting unit 3 of Embodiments 3 and the modification example of Embodiment 3 sets the evaluation region R1 at the place at which it is easy for gloss to occur in the face F of the subject with respect to the captured image input from the preprocessing unit 2, and sets the reference region R1a at the place at which it is difficult for the gloss to occur, similar to Embodiment 1, the analysis range can be set in three places, as illustrated in FIG. 10, in this embodiment, which is not particularly limited. For example, the chroma difference ($\Delta C^*$) and the lightness difference ($\Delta L^*$) can also be calculated on the basis of an image of a cheekbone portion (R1) and an image of a region (R1a) below an eye and beside a nose, and the unevenness index can also be calculated on the basis of an image of a forehead portion (R2). By setting a plurality of analysis ranges in this way, it is possible to acquire a higher accuracy evaluation regarding the luster and the oiliness.

The skin gloss evaluation device, the gloss evaluation method, and the gloss evaluation program according to all of the embodiments described above not only evaluate the gloss of the skin, but also can be used for a service for obtaining a correlation between the gloss (luster) of the skin and gloss of each material of the cosmetic materials in advance and providing the cosmetic materials to customers so that the customers can reproduce desired luster.

Example

An example in which gloss of the skin is evaluated using the gloss evaluation device of the present invention will be actually shown.

First, fifteen images obtained by variously changing gloss of a face image of a certain subject, that is, 15 levels of images were prepared. For each of the 15 images, the gloss of the skin was evaluated using the skin gloss evaluation device of the present invention. Further, using 15 images that are the same as such images, sensory evaluation according to luster and oiliness in a case where the face F of the subject in the image was viewed as a whole by ten observers was performed.

Figures 11A, 11B:
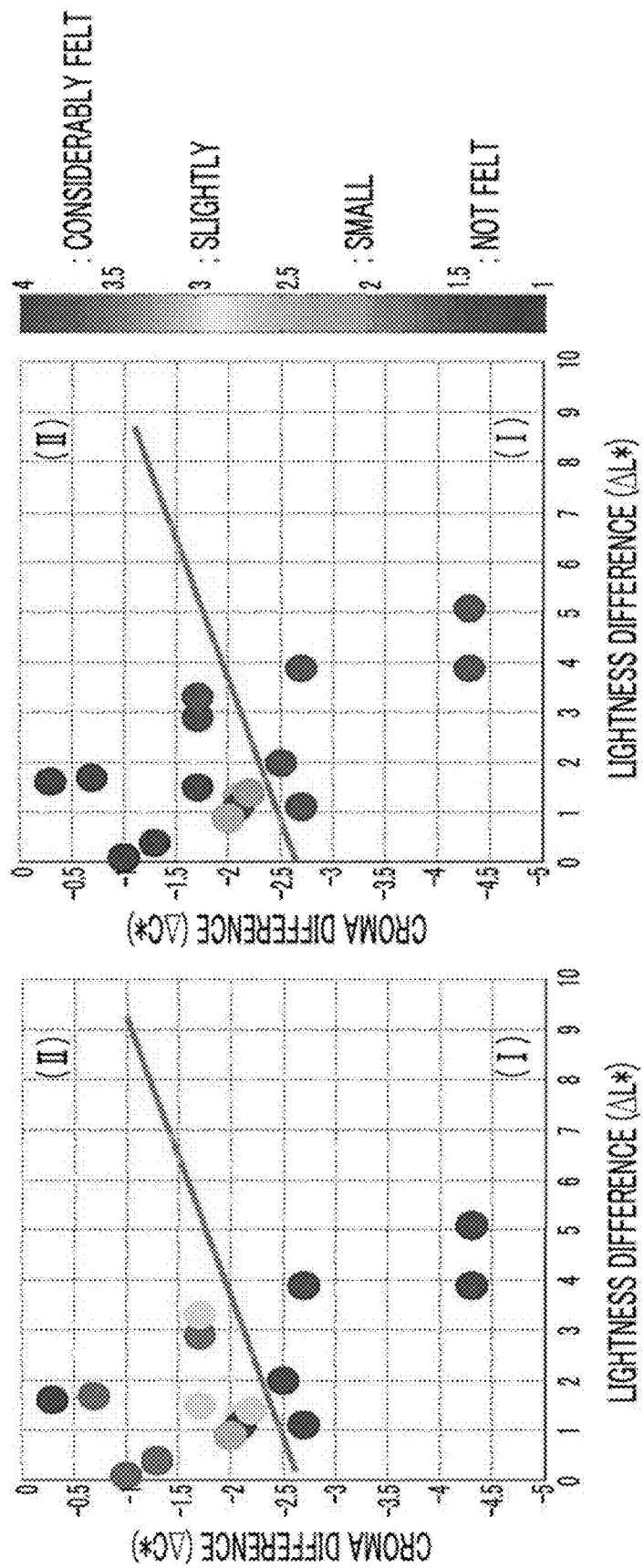

In FIGS. 11A and 11B, two skin evaluation indexes calculated using the skin gloss evaluation device of the present invention, that is, the chroma difference ($\Delta \times C^*$) and the lightness difference ($\Delta L^*$) are plotted, and each sensory evaluation result is shown as change in color. FIG. 11A illustrates a result of luster evaluation, and FIG. 11B illustrates a result of oiliness evaluation. Further, graphs shown in FIGS. 11A and 11B are functions calculated through discriminant analysis.

Here, the sensory evaluation value is an average value obtained by evaluating luster and oiliness feelings in four steps through sensory evaluation of the ten observers. In a case where the value approaches 1 (dark blue), it is evaluated that there are no luster and oiliness feelings, and in a case where the value approaches 4 (red), it is evaluated that there are the luster and oiliness feelings.

It can be seen from the chroma difference ($\Delta C^*$) and the sensory evaluation result that there is a sample in which oiliness is strongly felt and there is no sample in which luster is felt in a case where $\Delta C^*$ is a value greater than $-2.3$, and there are a small number of samples in which oiliness is felt and there are a large number of samples in which luster is felt in a case where $\Delta C^*$ is a value equal to or smaller than $-2.3$.

It was confirmed from this that whether the gloss of the skin is luster or oiliness can be specified on the basis of the chroma difference ($\Delta C^*$) according to the skin gloss evaluation device according to Embodiment 1.

Further, it can be seen that in a case where a plot based on the chroma difference ($\Delta C^*$) and the lightness difference ($\Delta L^*$) exists in (I) among two regions divided by a discriminant function $\Delta C^* = \frac{1}{6} \times \Delta L^* \times (-\frac{3}{8})$, that is, (I) and (II) in the figure, there are a large number of samples in which oiliness is strongly felt and there is no sample in which luster is felt at all. In a case where the plot exists in (II), there are a small number of samples in which oiliness is felt and there are a large number of samples in which luster is felt.

It can be confirmed from this that whether the gloss of the skin is luster or oiliness can be specified on the basis of the chroma difference ($\Delta C^*$) and the lightness difference ($\Delta L^*$) according to the skin gloss evaluation device according to Embodiment 2.

In FIGS. 12A and 12B, two skin evaluation indexes calculated using the gloss evaluation device of the present invention, that is, the unevenness index and the lightness difference ($\Delta L^*$) are plotted, and each sensory evaluation result is shown as change in color. FIG. 12A illustrates a result of luster evaluation, and FIG. 12B illustrates a result of oiliness evaluation.

It can be seen from the result of FIG. 12A that there are a large number of samples in which luster is not felt in a case where the unevenness index is greater than 1.0, there are a large number of samples in which luster is slightly felt and luster is considerably felt in a case where the unevenness index is equal to or greater than 0.93 and is equal to or smaller than 1.0, and there are samples in which little luster is felt in a case where the unevenness index is smaller than 0.93. That is, it can be seen that the luster is felt in a case where the unevenness index is in a predetermined range.

It can be seen from the result of FIG. 12B that there are a large number of samples in which oiliness is strongly felt in a case where the unevenness index is greater than 1.0, there are a large number of samples in which little oiliness is felt and oiliness is slightly felt in a case where the unevenness index is equal to or greater than 0.95 and is equal to or smaller than 1.0, and there is a sample in which oiliness is not felt in a case where the unevenness index is smaller than 0.95. That is, it can be seen that the oiliness is strongly felt in a case where the unevenness index is greater, and the oiliness is not felt in a case where the unevenness index is smaller.

On the basis of these results, it was confirmed that the luster and the oiliness of the skin can be quantitatively evaluated on the basis of the unevenness index according to the skin gloss evaluation device of Embodiment 3.

EXPLANATION OF REFERENCES

1: image input unit
2: preprocessing unit

3: analysis range setting unit
4: color space conversion unit
5, 5A to 5C: skin evaluation index calculation unit
6, 6A: luster and oiliness evaluation unit
7: display unit
8: control unit
9: operation unit
10, 20, 30, 40: skin gloss evaluation device
51: chroma calculation unit
52: lightness calculation unit
53: unevenness calculation unit
61: luster and oiliness determination unit
62: luster and oiliness quantifying unit
R1, R2: evaluation region
R1a: reference region
F: face
C: camera

What is claimed is:

1. A skin gloss evaluation device comprising:
an image input unit that inputs a captured image obtained by imaging a face of a subject;
an analysis range setting unit that sets a portion in which it is easy for gloss of skin of the subject to occur and a portion in which it is difficult for gloss to occur in the captured image as analysis ranges;
a skin evaluation index calculation unit that calculates a skin evaluation index related to the set of analysis ranges; and
a luster and oiliness evaluation unit that evaluates luster and oiliness of the face of the subject on the basis of the skin evaluation index,
wherein the skin evaluation index calculation unit calculates, as the skin evaluation index, a chroma difference between the portion in which it is easy for the gloss of the face of the subject to occur and the portion in which it is difficult for gloss to occur that are set as the analysis ranges, and
the luster and oiliness evaluation unit classifies and evaluates luster and oiliness on the basis of the chroma difference.

2. The skin gloss evaluation device according to claim 1,
wherein the skin evaluation index calculation unit further calculates, as the skin evaluation index, a lightness difference between the portion in which it is easy for the gloss of the face of the subject to occur and the portion in which it is difficult for gloss to occur that are set as the analysis ranges, and
the luster and oiliness evaluation unit classifies and evaluates the luster and the oiliness on the basis of the chroma difference and the lightness difference.

3. The skin gloss evaluation device according to claim 2,
wherein the skin evaluation index calculation unit converts an L* image of the portion in which it is easy for the gloss of the skin to occur that is set as the analysis range into information on a spatial frequency, weights the information on the spatial frequency with visual frequency characteristics of a human, and further calculates a total value of the weighted spatial frequency as an unevenness index, and
the luster and oiliness evaluation unit further evaluates intensity of luster or oiliness of the face of the subject on the basis of the unevenness index.

4. The skin gloss evaluation device according to claim 1,
wherein the skin evaluation index calculation unit converts an L* image of the portion in which it is easy for the gloss of the skin to occur that is set as the analysis range into information on a spatial frequency, weights the information on the spatial frequency with visual frequency characteristics of a human, and further calculates a total value of the weighted spatial frequency as an unevenness index, and
the luster and oiliness evaluation unit further evaluates intensity of luster or oiliness of the face of the subject on the basis of the unevenness index.

5. A skin gloss evaluation method comprising:
inputting a captured image obtained by imaging a face of a subject;
setting a portion in which it is easy for gloss of skin of the subject to occur and a portion in which it is difficult for gloss to occur in the captured image as analysis ranges;
calculating a skin evaluation index related to the set of analysis ranges; and
evaluating luster and oiliness of the face of the subject on the basis of the skin evaluation index,
wherein the skin gloss evaluation method further comprises:
calculating, as the skin evaluation index, a chroma difference between the portion in which it is easy for the gloss of the face of the subject to occur and the portion in which it is difficult for gloss to occur that are set as the analysis ranges; and
classifying and evaluating luster and oiliness on the basis of the chroma difference.

6. The skin gloss evaluation method according to claim 5, further comprising:
further calculating, as the skin evaluation index, a lightness difference between the portion in which it is easy for the gloss of the face of the subject to occur and the portion in which it is difficult for gloss to occur that are set as the analysis ranges; and
classifying and evaluating the luster and the oiliness on the basis of the chroma difference and the lightness difference.

7. The skin gloss evaluation method according to claim 6, further comprising:
converting an L* image of the portion in which it is easy for the gloss of the skin to occur that is set as the analysis range into information on a spatial frequency, weighting the information on the spatial frequency with visual frequency characteristics of a human, and calculating a total value of the weighted spatial frequency as an unevenness index; and
further evaluating intensity of luster and oiliness of the face of the subject on the basis of the unevenness index.

8. The skin gloss evaluation method according to claim 5, further comprising:
converting an L* image of the portion in which it is easy for the gloss of the skin to occur that is set as the analysis range into information on a spatial frequency, weighting the information on the spatial frequency with visual frequency characteristics of a human, and calculating a total value of the weighted spatial frequency as an unevenness index; and
further evaluating intensity of luster and oiliness of the face of the subject on the basis of the unevenness index.

9. A non-transitory computer readable recording medium storing a skin gloss evaluation program comprising:
an image input step of inputting a captured image obtained by imaging a face of a subject;
an analysis range setting step of setting a portion in which it is easy for gloss of skin of the subject to occur and a portion in which it is difficult for gloss to occur in the captured image as analysis ranges;

a skin evaluation index calculation step of calculating a skin evaluation index related to the set analysis ranges; and a luster and oiliness evaluation step of evaluating luster and oiliness of the face of the subject on the basis of the skin evaluation index, wherein the skin evaluation index calculation step includes calculating, as the skin evaluation index, a chroma difference between the portion in which it is easy for the gloss of the face of the subject to occur and the portion in which it is difficult for gloss to occur that are set as the analysis ranges, and the luster and oiliness evaluation step includes classifying and evaluating luster and oiliness on the basis of the chroma difference.

10. The non-transitory computer readable recording medium storing the skin gloss evaluation program according to claim 9, wherein the skin evaluation index calculation step includes further calculating, as the skin evaluation index, a lightness difference between the portion in which it is easy for the gloss of the face of the subject to occur and the portion in which it is difficult for gloss to occur that are set as the analysis ranges, and the luster and oiliness evaluation step includes classifying and evaluating the luster and the oiliness on the basis of the chroma difference and the lightness difference.

11. The non-transitory computer readable recording medium storing the skin gloss evaluation program according to claim 10, wherein the skin evaluation index calculation step includes converting an L* image of the portion in which it is easy for the gloss of the skin to occur that is set as the analysis range into information on a spatial frequency, weighting the information on the spatial frequency with visual frequency characteristics of a human, and calculating a total value of the weighted spatial frequency as an unevenness index, and the luster and oiliness evaluation step includes further evaluating intensity of luster and oiliness of the face of the subject on the basis of the unevenness index.

12. The non-transitory computer readable recording medium storing the skin gloss evaluation program according to claim 9, wherein the skin evaluation index calculation step includes converting an L* image of the portion in which it is easy for the gloss of the skin to occur that is set as the analysis range into information on a spatial frequency, weighting the information on the spatial frequency with visual frequency characteristics of a human, and calculating a total value of the weighted spatial frequency as an unevenness index, and the luster and oiliness evaluation step includes further evaluating intensity of luster and oiliness of the face of the subject on the basis of the unevenness index.

* * * * *